United States Patent [19]

May et al.

[11] Patent Number: 4,992,738

[45] Date of Patent: Feb. 12, 1991

[54] DEVICE FOR THE MEASURING OF GAS, VAPOR OR AEROSOL FRACTIONS OF A MEASURED GAS

[75] Inventors: Wolfgang May, Reinfeld; Johannes Heckmann, Lübeck, both of Fed. Rep. of Germany

[73] Assignee: Drägerwerk Aktiengesellschaft, Lubeck, Fed. Rep. of Germany

[21] Appl. No.: 341,579

[22] Filed: Apr. 21, 1989

[30] Foreign Application Priority Data

May 4, 1988 [DE] Fed. Rep. of Germany ....... 3815131

[51] Int. Cl.5 ............................................. G01N 27/28
[52] U.S. Cl. .................................. 324/450; 73/27 R; 204/1 T; 204/400; 204/153.1; 324/439; 324/446; 324/705; 324/724
[58] Field of Search ............... 324/438, 439, 446, 450, 324/447, 449, 65 R, 425, 65 P, 464, 466, 467, 691, 705, 706, 722, 724; 73/27 R, 23; 340/632; 204/1 T, 406, 400

[56] References Cited

U.S. PATENT DOCUMENTS

| 993,586 | 5/1911 | Digby et al. | 324/447 |
|---|---|---|---|
| 3,100,868 | 8/1963 | McAfee, Jr. | 324/466 |
| 3,223,608 | 12/1965 | Hersch | 324/439 X |
| 3,447,071 | 5/1969 | Webb | 324/464 |
| 3,738,812 | 6/1973 | Berrt et al. | 324/439 X |
| 3,838,971 | 10/1974 | Albertson | 204/431 X |
| 3,961,898 | 6/1976 | Frenyo | 324/439 X |
| 3,966,579 | 6/1976 | Chang et al. | 324/439 X |
| 4,017,792 | 4/1977 | Heiland et al. | 73/27 R X |
| 4,123,700 | 10/1978 | LaConti et al. | 324/425 |
| 4,473,456 | 9/1984 | Hawkins | 324/439 X |
| 4,477,778 | 10/1984 | Lawrence, Jr. et al. | 324/466 |
| 4,713,618 | 12/1987 | Carlson et al. | 324/450 X |

FOREIGN PATENT DOCUMENTS

1368870 10/1974 United Kingdom.

*Primary Examiner*—Reinhard J. Eisenzopf
*Assistant Examiner*—Robert W. Mueller
*Attorney, Agent, or Firm*—McGlew & Tuttle

[57] ABSTRACT

For the measurement of gas, vapor, or aerosol fractions of a measured gas, the fraction to be determined is absorbed in a reaction solution, and a change of resistance from a reaction between the fraction and the reaction solution is determined as the measured variable by an ohmmeter, using electrodes in the reaction solution. The measured gas entering a test container through a sealing unit tight to the reaction solution and passing the medium to be determined, is improved with regard to all-purpose use and convenient measurement. This is done pursuant to the invention by placing the reaction solution in a disposable test container that can be inserted or connected interchangeably to the measuring device which has electrodes. The test container is sealed, at least at one end, with a sealing unit that is permeable to the medium to be determined and impermeable to the reaction solution.

21 Claims, 3 Drawing Sheets

DEVICE FOR THE MEASURING OF GAS, VAPOR OR AEROSOL FRACTIONS OF A MEASURED GAS

BACKGROUND OF THE INVENTION

1. Field of the Invention

This invention particularly concerns a device for the measurement of a gas, including a vapor, or aerosol fractions of a measured gas. The fraction to be determined is absorbed in a reaction solution and a change of resistance of the reaction solution because of a reaction between the fraction and the reaction solution is measured as the measured parameter by an ohmmeter, using electrodes in the reaction solution. The measured gas enters a test container through a sealing unit that is tight to the reaction solution and passes the medium to be determined.

A measuring device with an electrolytic cell is described in U.S. Pat. No. 3,838,971. There are two electrodes in the electrolytic cell in a solution of sulfuric acid or phosphoric acid. This electrolyte is exposed to an atmosphere of the gas to be measured, with the alcohol concentration in human breath being intended as the fraction of the measured gas to be determined. The electrical conductivity of the cell is determined by an ohmmeter and the fraction of alcohol concentration is thus determined.

A measuring device of the type with a test container that has electrodes and electrical connections for connecting to an ohmmeter, is disclosed by German Patent No. 21 47 718 in the monitoring of the carbon dioxide content in the circulatory system for inhalation anesthesia.

SUMMARY OF THE INVENTION

This invention effects the determination of fractions of a measured gas by resistance measurement in an electrolytic cell so that the measurement can be made especially easily and with fast changes of the subject matter being examined.

According to the invention, a reaction solution is placed in a disposable container that is inserted interchangeably in a measuring device, which holds electrodes and is sealed at least at one end with a sealing unit that is tight to the reaction solution but passes the medium to be determined.

The measurement is substantially facilitated by the use of interchangeable test containers. It is beneficial to design the test containers as test tubes or disk-shaped cuvettes.

Such test containers as test tubes or disk-shaped cuvettes advantageously are provided with electrodes that can be connected to the measuring device.

In another design that is beneficial, the test container has a puncturable septum at least at one end for introducing an electrode connected to the measuring device. The electrodes in this case can beneficially be located permanently in the measuring device, and the test container is inserted into the measuring device in such a way that needle-shaped electrodes, for example, each perforate a septum of the test container, for example a rubber-like, piercable sealing film. This brings the electrodes into contact with the reaction solution as an electrolyte cell to the ohmmeter, for example to a directly indicating conductimeter.

The test tube is beneficially designed as a diffusion tube, preferably with plugs as seals at both ends that are impervious to the reaction solution and pass the medium to be detected, with the two electrodes being displaced from one another in the longitudinal direction of the test tube.

In a suitable alternative design, the test tube is designed for forced flow and is connected to a feed junction for connection to a feed device, for example, a suction or pressure pump for feeding the measuring gas.

Another particularly desirable design for forced flow through the test tube provides for the test tube to be sealed at both ends with plugs that are tight to the reaction solution and pass the measured gas and the medium to be determined, and for the two electrodes to be located inside the test tube, opposite one another and perpendicular to the longitudinal direction. The choice between the electrode systems separated in the longitudinal direction of the test tube and those opposite one another perpendicular to the longitudinal direction depends on the internal resistance of the reaction solution and on its change from the reaction of a measured gas to be determined.

Additional improvements can optionally be achieved by providing the test container, i.e., the test tube or the disk-shaped cuvette, with a bar code for the automatic reading of the relevant parameter values in the measuring device. Various initial values for the electrolytic cells that vary in the mass production of test containers (such as type of gas, production batch, limits, etc.), can be read automatically in an evaluator or even when inserting the test container into the measuring device, and can be taken appropriately into consideration.

A suitable device for the measurement of gas, vapor, or aerosol fractions of a measured gas, in which the fraction to be determined is aborbed in a reaction solution, and in which a change of resistance of the reaction solution because of a reaction between the fraction and the reaction solution is determined as the measured value by an ohmmeter, using electrodes in the reaction solution, can be supplied with such a reaction solution that contains a substance that reacts with the fraction to be determined and forms a reaction product, which in turn changes the conductivity by reacting with the reaction solution. Such a reaction solution can be used not only with interchangeable test containers, but basically in general, when using ohmmeters for electrolytic cells loaded with gas, vapor, or aerosol. Fractions of a measured gas that do not directly bring about a change of resistance, but only produce an effect as a change of resistance or of conductivity through a reaction product occurring as an intermediate, can also be determined by the selection of an appropriate substance.

As an example of a reaction solution that contains a substance that reacts with the fraction to be determined and forms a reaction product, which in turn changes the conductivity by reacting with the reaction solution is the reaction between hydrochloric acid and sodium hydroxide solution according to the reaction equation $HCl + NaOH \; NaCl + H_2O$.

Another beneficial rule for the choice of a reaction solution that can be applied independently of the interchangeable test containers, may comprise this reaction solution containing a strongly dissociated substance that forms a slightly dissociated compound with the fraction to be determined.

An example of this is the reaction between ammonia, sodium hydroxide solution, and potassium mercuric iodide according to the equation:

$$NH_3 + 3NaOH + 2K_2(HgI_4) \rightarrow (Hg_2N)I \cdot H_2O + 2H_2O + 4KI + 3NaI$$

With this method, it also is appropriate to select the substance so that the slightly dissociated compound is essentially insoluble in the reaction solution and precipitates. An example of such a compound is the reaction between hydrochloric acid and silver nitrate, or between sulfur dioxide, barium hydroxide, and water according to the following equations:

$$HCl + AgNO_3 \rightarrow AgCl + HNO_3$$

$$SO_2 + Ba(OH)_2 + H_2 \rightarrow BaSO_4 + 2H_2O.$$

Another alternative method that is suitable can provide for a choice of the substance such that the slightly dissociated compound remains soluble in the reaction solution, but with the fraction of dissolved ions and thus the resistance of the electrolytic cell changing. An example of this is the reaction between acetone and hydrazine according to the equation:

$$(CH_3)_2-C=O + NH_2 \rightarrow (CH_3)_2-C=NNH_2 + H_2O$$

Accordingly, it is an object of the invention to provide a method of measuring a medium as a gas, a gas vapor and an aerosol fraction of a gas using a reactant material which reacts with the medium by a change in resistance and prefereably a disposable container as well as an ohmmeter or resistance measuring device which has two spaced-apart electrode terminals and which comprises putting the reactant material in a container and placing the electrode terminals in a container in spaced-apart locations in the reactant material, sealing the container in respect to the reactant material for permitting the passage of the medium to be measured and noting the change of the ohmmeter.

A further object of the invention is to provide a device for measuring a fraction of a gas medium which comprises a container which is preferably disposable having a reactant material therein which is sealed against the passage of the reactant material out of the container, but permits the material to be discovered to pass therethrough and which includes terminal means positionable in the reactant material to a device for measuring the change of resistance of the material as an indication of the percentage of presence of the medium to be detected.

A further object of the invention is to provide a device for measuring fractions of a medium which is passed through a reactant material in a testing tube and which is simple in design, rugged in construction and economical to manufacture.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive matter in which preferred embodiments of the invention are illustrated.

Figure 1:
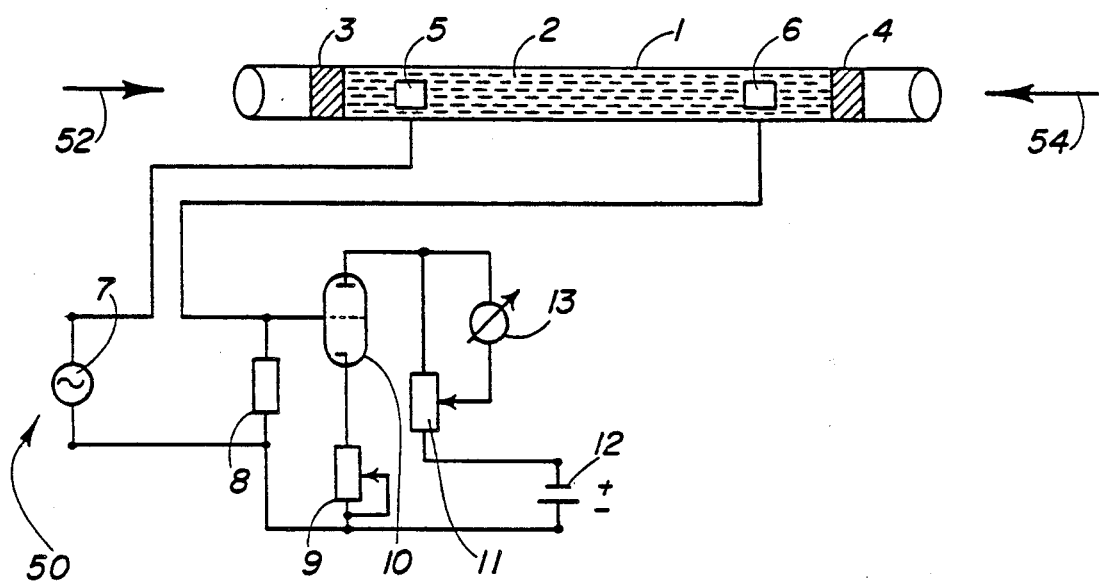
FIG. 1 is a schematic view of a measuring device with a diffusion test tube constructed in accordance with the invention.

Referring to the drawings, in particular, the invention embodied therein comprises a method of measuring a medium such as a gas, a gas vapor and an aerosol which form fractions of a gas using a disposable container 1 and an ohmmeter or measuring device generally designated 50 for determining the change of resistance in a reactant material 2 placed in the disposable container 1. In accordance with the invention, the container 1 is sealed by plugs 3 and 4 which are such as to contain the reactant material 2 therein against removal, but to permit passage of the material to be measured. The measuring device 50 includes terminals 5 and 6 which are placed in spaced relationship in the reactant material 2 and the change of resistance on the detection device 50 is noted as an indication of the medium to be determined.

FIG. 1 illustrates a diffusion tube 1 as a disposable part or test container for measuring gas, vapor, or aerosol fractions of a measured gas diffusing in at both ends in the direction of the arrows 52 and 54. The diffusion tube 1 is sealed at both ends with respective plugs 3 and 4 made of PTFE (polytetrafluoroethylene) that are permeable to the gaseous medium to be measured but impermeable to the reaction solution 2. The two electrodes 5 and 6 are displaced at a distance from one another in the long direction of the test tube 1. The electrodes 5 and 6 are connected to a measuring device 50 such as conductimeter, shown in simplified illustration.

The measuring device 50 includes a pulse generator 7 that generates a sequence of positive and negative voltage pulses with grid leak resistor 8 and a cathode leak resistor 9 are associated with a triode 10, whose anode is connected to a source of anode voltage 12 through an anode resistor 11. The input voltage on the grid of the triode 10, modified by the effect of the change of resistance between the electrodes 5, 6 of the test tube 1, changes the anode current with corresponding amplification, which can be tapped adjustable at the anode resistor 11 with a tap through the indication instrument 13 to determine the measured variable.

The test tube in the embodiment intended for practical use is approximately 10 cm long and has a diameter of 1 cm. To measure hydrogen chloride gas, the reaction solution used as an electrolyte comprises a silver nitrate solution, and the two electrodes 5 and 6 comprise a platinum and are placed at a distance of about 6 cm from one another.

Figure 2:
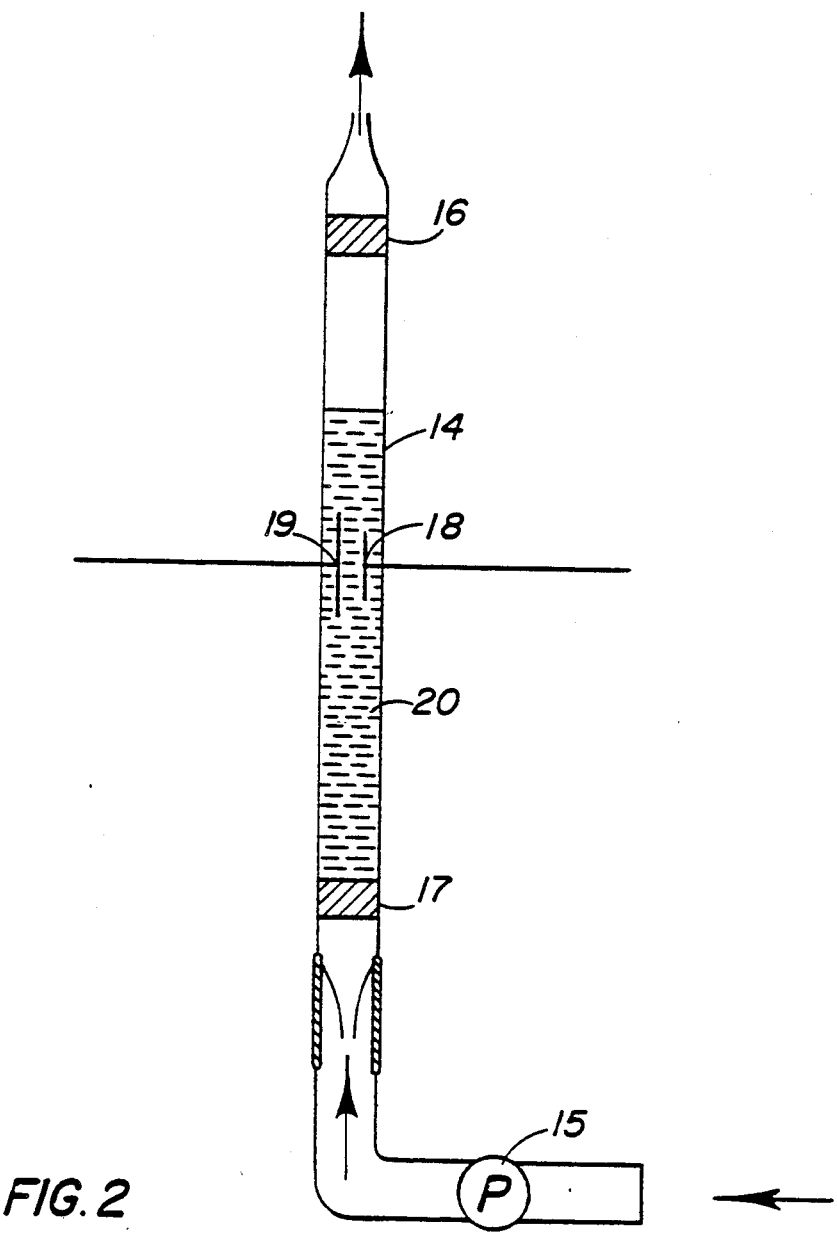
FIG. 2 is a similar view of another embodiment of a measuring device with forced flow test tube.

In the design of FIG. 2, a disposable test tube 14 is provided, which is connected to a feed device or pump 15 by a plug-in connector for the forced flow. Porous plugs at each end are labelled 16 and 17, and two electrodes 18 and 19 in this case are opposite one another perpendicular to the long direction of the test tube 14. The electrodes 18 and 19 are connected to a conductimeter 50 as shown in FIG. 1. The reaction solution 20 is beneficially loaded into the test tube used in a vertical position, so that about ⅔ of the volume of the tube is filled.

Figure 3:
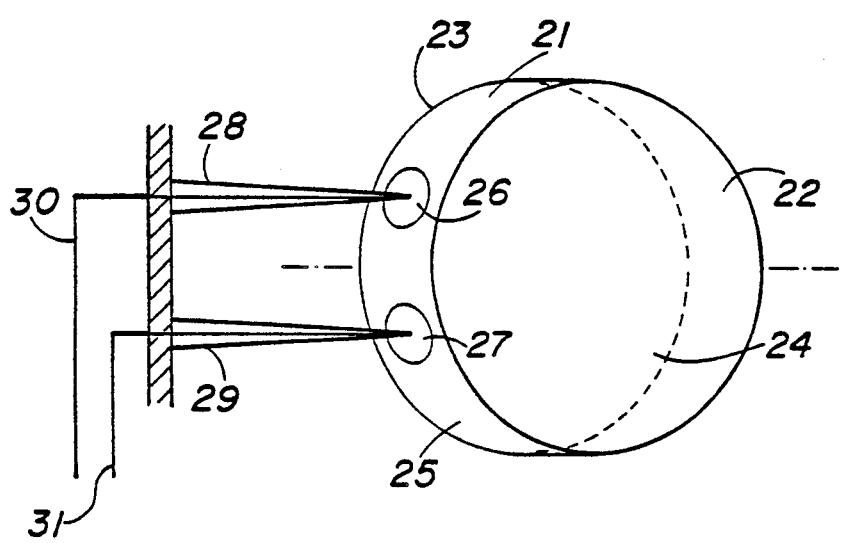
FIG. 3 is a view similar to FIG. 1 of another embodiment with a disk-shaped cuvette with puncturable septa.

In the design of FIG. 3, a disposable disk-shaped cuvette 21 is provided as the test container. It is sealed on the front and back with membrane films 22,23 permeable to the fraction to be determined. The cavity in the test cuvette 21 is filled with a reaction solution 24. There are flexible seals 26 and 27 in the rim area 25 of the test couvette 21, that are perforated as puncturable septa by needle-shaped electrodes 28 and 29 when the test cuvette 21 is pressed into corresponding mounts in the measuring device. The connecting lines 30, 31 are connected in a known way to a conductimeter 50, for example according to FIG. 1. Since the needle-shaped electrodes 28 and 29 have conductive sections only at their tips, constant electrode transition resistance compared to the reaction solution used as electrolyte are produced with sufficient depth of penetration.

While specific embodiments of the invention have been shown and described in detail to illustrate the application of the principles of the invention, it will be understood that the invention may be embodied otherwise without departing from such principles.

What is claimed is:

1. A device for measuring the gas, vapor and aerosol fractions of a gas whose characteristic is to be determined, comprising a disposable test container interchangeably connected to said device, a reaction solution in said test container of a character which will change in resistance based on a reaction between the reaction solution and the gas to be determined, a detection means for determining change of resistance of the reaction solution including spaced-apart terminals which are positioned in the reaction solution, and means for sealing said test container on at least one end comprising a material which permits passage of the gas to be detected, but which prevents passage of the reaction solution.

2. A device according to claim 1, wherein said test container comprises a test tube.

3. A device according to claim 2, wherein said test tube is vertically elongated and said electrodes extend in a vertical plane at spaced locations from each other and in opposition to each other.

4. A device according to claim 2, wherein said test tube comprises a force flow container having a feed junction for connection to a feed device.

5. A device according to claim 1, wherein said test container comprises a disk-shaped cuvette.

6. A device accoring to claim 1, wherein said test container includes electrodes which may be connected to said measuring device.

7. A device according to claim 1, wherein said test container comprises a member having a portion comprising a puncturable septum providing means for introducing an electrode into said test container.

8. A device according to claim 1, wherein said test container comprises a diffusion tube.

9. A device according to claim 8, wherein said diffusion tube includes a plug at each end which seal the reaction solution in said test container and wherein said electrodes of said detection means are located at spaced longitudinal locations in said tube.

10. A device according to claim 1, wherein said test container has bar codes for the automatic reading of relevant parameter values in the measuring device.

11. A device according to claim 1, wherein said electrodes are positioned in the reaction solution and said solution contains a substance that reacts with the fraction of the gas medium to be determined and forms a reaction product which changes the conductivity by reacting with the reaction solution.

12. A device according to claim 11, wherein the substance is chosen so that a small dissociated compound is essentially insoluble in the reaction solution and precipitates.

13. A device according to claim 11, wherein the substance is chosen so that a little dissociated compound remains soluble in the reaction solution with the fraction of dissolved ions changing.

14. A device according to claim 1, wherein the reaction solution contains a strongly dissociated substance that forms a compound with a fraction to be determined that dissociates only slightly.

15. A method of measuring a medium such as a gas, gas vapor and an aerosol fraction of a gas using a reaction solution which reacts with the medium by a change in resistance and a disposable container and an ohmmeter having electro terminals, comprising (a) putting the reaction solution in said container, (b) placing said electro terminals in said container at spaced-apart locations of the reaction solution, (c) sealing said container in respect to the reaction solution while permitting the passage of the medium to be measured, (d) noting the change of the ohmmeter, (e) replacing said container with a new disposable container and (f) repeating steps (a) through (d), inclusive.

16. A method according to claim 15, wherein the gas reactant solution is sealed within the container but the container includes means for the passage of the material to be measured.

17. A device for measuring the gas, vapor and aerosol fractions of a gas whose characteristic is to be determined, comprising a disposable test container interchangeably connected to said device, a reaction solution in said test container of a character which will change in resistance based on a reaction between the reaction solution and the gas to be determined, a detection means for determining change of resistance of the reaction solution including spaced-apart terminals which are positioned in the reaction solution and a voltage source and ohmmeter connected across said terminals, and means for sealing said test container on at least one end comprising a material which permits passage of the gas to be detected, but which prevents passage of the reaction solution.

18. A device for measuring the gas, vapor and aerosol fractions of a gas whose characteristic is to be determined, comprising a test container, a reaction solution in said test container of a character which will change in resistance based on a reaction between the reaction solution and the gas to be determined, means for sealing said test container on at least one end comprising a material which permits passage of the gas to be detected, but which prevents passage of the reaction solution, and a detection means for determining change of resistance of the reaction solution comprising a pair of electrodes which are positioned at spaced-apart locations of the reaction solution, means for generating a sequence of positve and negative voltage pulses connected to one of said electrodes, an ohmmeter and a triode having an anode and a grid connected respectively in series circuit with said ohmmeter and the other of said electrodes, the arrangement being such that any change in resistance of the reaction solution will produce a corresponding change in the input voltage to said grid, said change in input voltage producing in turn a corresponding change in anode current which can be measured by said ohmmeter.

19. A device for measuring the gas, vapor and aerosol fractions of a gas whose characteristic is to be determined, comprising an elongated diffusion tube interchangeably connected to said device, a reaction solution in said diffusion tube of a character which will change in resistance based on a reaction between the reaction solution and the gas to be determined, said diffusion tube including a plug at each end which seal the reaction solution within said tube, a detection means for determining change of resistance of the reaction solution including a pair of electrodes which are positioned in spaced longitudinal locations in said diffusion tube and an ohmmeter connected across said electrodes, said diffusion tube further including a feed junction for connection to a feed device for forcing the flow of gas through said tube.

20. A device for measuring the gas, vapor and aerosol fractions of a gas whose characteristic is to be determined, comprising a vertically elongated diffusion tube interchangeably connected to said device, a reaction solution in said diffusion tube of a character which will change in resistance based on a reaction between the reaction solution and the gas to be determined, said diffussion tube including a plug at each end which seal the reaction solution within said tube, a detection means for determining change of resistance of the reaction solution including a pair of electrodes which extend in a vertical plane opposite to one another at spaced locations in said diffusion tube and an ohmmeter connected across said electrodes, said diffusion tube further including a feed junction for connection to a feed device for forcing the flow of gas through said tube.

21. A device for measuring the gas, vapor and aerosol fractions of a gas whose characteristic is to be determined, comprising a disk-shaped cuvette interchangeably connected to said device, a reaction solution in said cuvette of a character which will change in resistance based on a reaction between the reaction solution and the gas to be determined, said cuvette having side walls provided with puncturable septums and a membrane film positioned to the front and back sides thereof which seal the reaction solution within said cuvette while permitting the passage of the gas to be detected, and a detection means for determining change of resistance of the reaction solution including a pair of electrodes which extend through said puncturable septums in spaced apart relation in said cuvette and an ohmmeter connected across said electrodes.

* * * * *